United States Patent [19]
Izawa

[11] Patent Number: 6,008,054
[45] Date of Patent: *Dec. 28, 1999

[54] METHOD OF MEASURING A β-GLUCAN

[75] Inventor: Masayuki Izawa, Yaizu, Japan

[73] Assignee: Sapporo Breweries Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/737,805

[22] PCT Filed: Mar. 29, 1996

[86] PCT No.: PCT/JP96/00846

§ 371 Date: Nov. 27, 1996

§ 102(e) Date: Nov. 27, 1996

[87] PCT Pub. No.: WO96/30756

PCT Pub. Date: Oct. 3, 1996

[30] Foreign Application Priority Data

Mar. 29, 1995 [JP] Japan .................................. 7-94177
Dec. 27, 1995 [JP] Japan ................................. 7-351193

[51] Int. Cl.$^6$ .................................................. G01N 30/02
[52] U.S. Cl. .............................. 436/52; 436/91; 436/93; 436/94; 436/161; 436/172
[58] Field of Search ............................. 436/161, 52, 172, 436/94, 93, 91

[56] References Cited

U.S. PATENT DOCUMENTS

| | | |
|---|---|---|
| 4,902,568 | 2/1990 | Morohoshi . |
| 5,234,836 | 8/1993 | Nokihara et al. ......................... 436/89 |
| 5,242,812 | 9/1993 | Even-Chen . |
| 5,302,695 | 4/1994 | Frank et al. . |
| 5,374,550 | 12/1994 | Smith et al. . |
| 5,585,274 | 12/1996 | Izawa ....................................... 436/52 |

OTHER PUBLICATIONS

Manzanares et al. J. Cereal Science vol. 18, No. 3, Nov. 1993 pp. 211–223.

Miller, Chromatography: Concepts and Contrasts, John Wiley & Sons, 1988, pp. 25–27.

Biorad Catalog, "Chromatography Electrophoresis Immunochemistry Molecular Biology HPLC" p. 38, Mar. 1990.

Schweitzer (Editor) Handbook of Separation Techniques for Chemical Engineers (McGraw–Hill, Inc) p. 2–6, 1979.

Foldager et al., Carlsberg Res. Commun. (1984), 49 (5) pp. 525–534.

Chemical Abstracts CA 116:37232, Kristensen et al., Thromb. Res. (1991), 64(2), 131–41.

Chemical Abstracts CA 112:159368, Wu et al., J. Liq. Chromatogr. (1989), 12(15), 2901–18.

Suortti, J. Chromatogr. (1993), 632(1–2), pp. 105–110.

Wood et al., Cereal Chem. (1991), 68(5), pp. 530–536.

Manzanares et al., J. Invest. Brew. (1991), 97(2), pp. 101–104.

*Primary Examiner*—Jan Ludlow
*Attorney, Agent, or Firm*—Oblon, Spivak, McClelland, Maier & Neustadt, P.C.

[57] ABSTRACT

For the purpose of improving the accuracy and reproducibility of the measurement of β-glucan by flow injection method using calcofluor, the present invention provides a method in which a gel filtration column having the volume of the interstice outside of the gel particles which is not larger than the column effluent volume within a certain period of time and the column content volume which is 10 times or more as large as the sample injection volume is placed between the sample injection port and the detector in said system.

6 Claims, 4 Drawing Sheets

METHOD OF MEASURING A β-GLUCAN

FIELD OF TECHNOLOGY

The present invention relates to a method for measuring β-(1,3) (1,4)-D-glucan (hereinafter referred to as β-glucan) and, more precisely, to a method for measuring β-glucan which is in various cereals such as barley, etc. and in malt, wort, beer, etc.

BACKGROUND TECHNOLOGY

Calcofluor which is represented by the following structural formula is a fluorescent compound which specifically binds to β-glucan to have an increased degree of fluorescent intensity due to the binding. Jorgensen et al of Carlsberg Co. in Denmark have reported a flow injection method using this compound (Carlsberg Res. Commun., Vol. 53, pp.277–285, 1988; Analytica-EBC, 3.11.2).

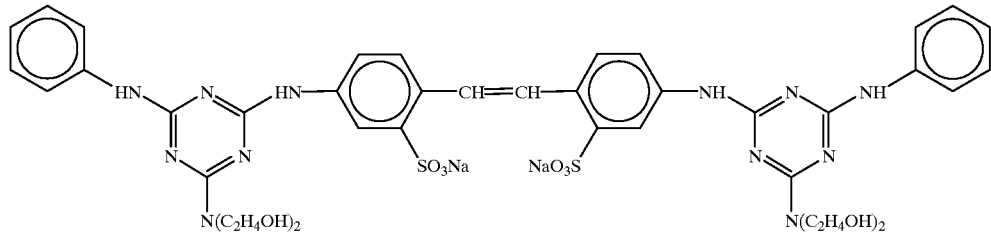

Some other researchers have also reported a flow injection method using calcofluor on the basis of the same principle (Journal of the Institute of Brewing, Vol. 95, p.327, 1989; Journal of the Institute of Brewing, Vol.93, p.396, 1987). Recently, commercial flow injection system using calcofluor have been marketed by Tecator Co. in Sweden and by Fiatron Co. in USA (Journal of American Society of Brewing Chemists, Vol. 93, p.396, 1987).

These are all applied system from the system shown in FIG. 1 or FIG. 2, in which a flow of a sample or a solution containing a sample is mixed with a flow of a reagent solution prepared by dissolving β~35 mg/liter of calcofluor in a tris or glycine buffer (pH 8 to 10) by which calcofluor is bound to β-glucan in the sample, using a suitable tube, and the increase in the fluorescent intensity of the thus-bonded compound is measured using a fluorescence detector.

To determine the β-glucan content in the sample such as wort, beer, etc. by these methods, a solution containing a known concentration of purified β-glucan extracted from barley is used as a standard.

However, such conventional flow injection methods using calcofluor were reported to involve fluctuation of the measured values due to the effects of sugars in the sample wort or ethanol in beer which also vary depending on the measurement conditions such as sample injection volume and empty volume of the mixing zone, resulting in variation in β-glucan content even in an identical sample.

In addition, lower molecule components (saccharides, ethanol, etc.) having inhibitory effect on fluorescent reaction of calcofluor were found recently to be present in wort or beer, and the contents of such components in wort or beer were found to vary depending on the species and amount of the malts employed.

It is obvious that the above-mentioned substances hindering fluorescent reaction of calcofluor such as saccharides, ethanol, etc. cause errors in the measurement of the β-glucan content in wort or beer by the conventional flow injection methods using calcofluor.

Accordingly, to establish a system which cannot be affected by saccharides, ethanol and hindering substances of calcofluor fluorescent reaction present in a sample to be measured is essential for the purpose of improving the accuracy of β-glucan measurement, and such system is desired to be developed.

Thus, an objective of the present invention is to improve the accuracy and reproducibility of the measurement of β-glucan by the flow injection methods using calcofluor, by means of establishing the system and measurement condition in which a short gel filtration column is employed to allow high molecular β-glucan having a molecular weight of 10,000 or higher to be passed through without being retained in the column support while low molecular saccharides, ethanol and substances hindering fluorescent reaction of calcofluor are retained by gel particles as column support for a period of several seconds to several ten seconds, whereby achieving elution as separated from β-glucan.

In addition, optimization of the column size to achieve an analysis time equivalent to that in the analysis without such column (several minutes (preferably 3 minutes) or shorter) is another objective of the present invention.

A method for measuring β-glucan by a flow injection system using calcofluor according to the present invention employs a method wherein a sample flow is passed through a gel filtration column by which it is possible that after injecting the sample into the flow of an eluent an analysis target, namely, high molecular β-glucan having a molecular weight of 10,000 or higher is eluted within a certain period (within several minutes (preferably 3 minutes)) while the elution of low molecular components such as maltose, ethanol and substances hindering fluorescent reaction of calcofluor is retarded in relation to the elution of high molecular β-glucan, whereby separating β-glucan from the components causing fluctuation of the measured values, and the sample thus having been passed through the column was then measured by a fluorescence detector.

As mentioned above, the present invention is a method for measuring β-glucan wherein a gel filtration column is placed between the sample injection port and the detector in the system, said column being characterized in that the volume of the interstice outside of the gel particles (void volume) is not larger than the volume of the fluid eluted from the column within a certain time period (preferably 3 minutes) and the column content volume (the volume of the interstice outside of the gel particles plus the volume of the solvent within the gel particles (inner volume)) corresponding to the volume of the eluent with which the low molecular substance migrating into the network of the gel particles are eluted from the column is 10 times or more as large as the sample injection volume, whereby achieving that the analysis target high molecular β-glucan does not migrate into the network of the gel particles but can readily be eluted from the column when the eluent in the volume equal to the total volume of the interstice of the gel particles is passed through the interstice of the gel particles.

When the column content volume mentioned above is smaller than the sample injection volume, satisfactory separation between high molecular β-glucan having a molecular weight of 10,000 or higher and low molecular saccharides, ethanol and substances hindering fluorescent reaction of calcofluor can not be achieved.

DISCLOSURE OF THE INVENTION

Accordingly, the present invention relates to a method for measuring β-glucan by a flow injection system using calcofluor, in which a gel filtration column having the volume of the interstice outside of the gel particles which is not larger than the column effluent volume within a certain time period and the column content volume which is 10 times or more as large as the sample injection volume is placed between the sample injection port and the detector in said system.

Figure 1:
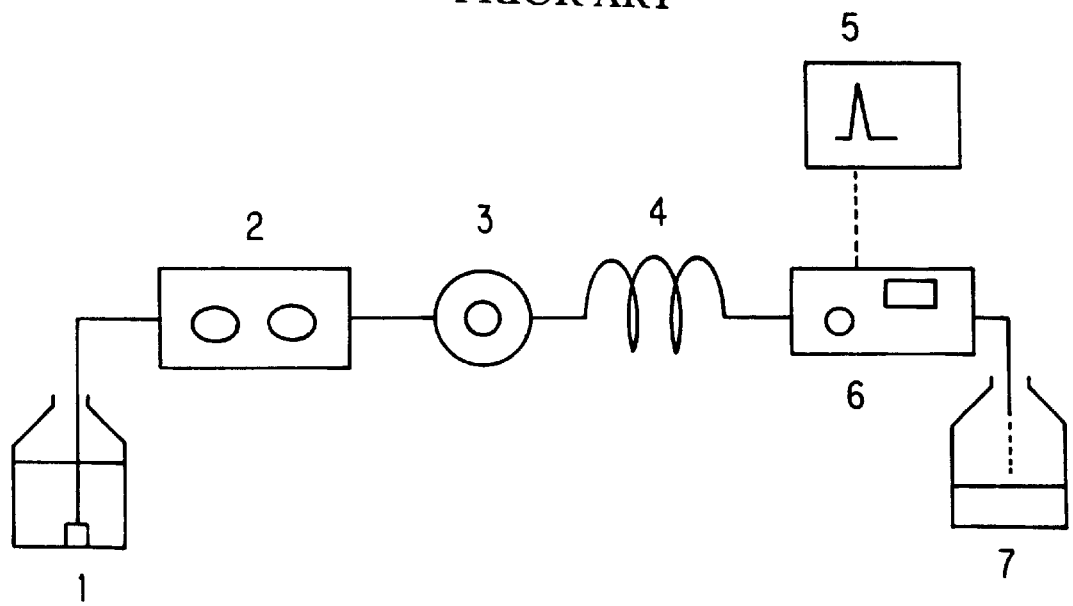
FIG. 1 shows one conventional system for measuring β-glucan content by a flow injection method using calcofluor.

As shown in the figures, calcofluor reaction fluid 1, pump 2, sample injector 3, reaction zone 4, integrator 5 (for data processing, such as quantification from detected signals), fluorescent detector 6, waste fluid 7, buffer or distilled water 8 and gel filtration column 9 are provided in the system.

BEST MODE TO PRACTICE THE INVENTION

Figure 2:
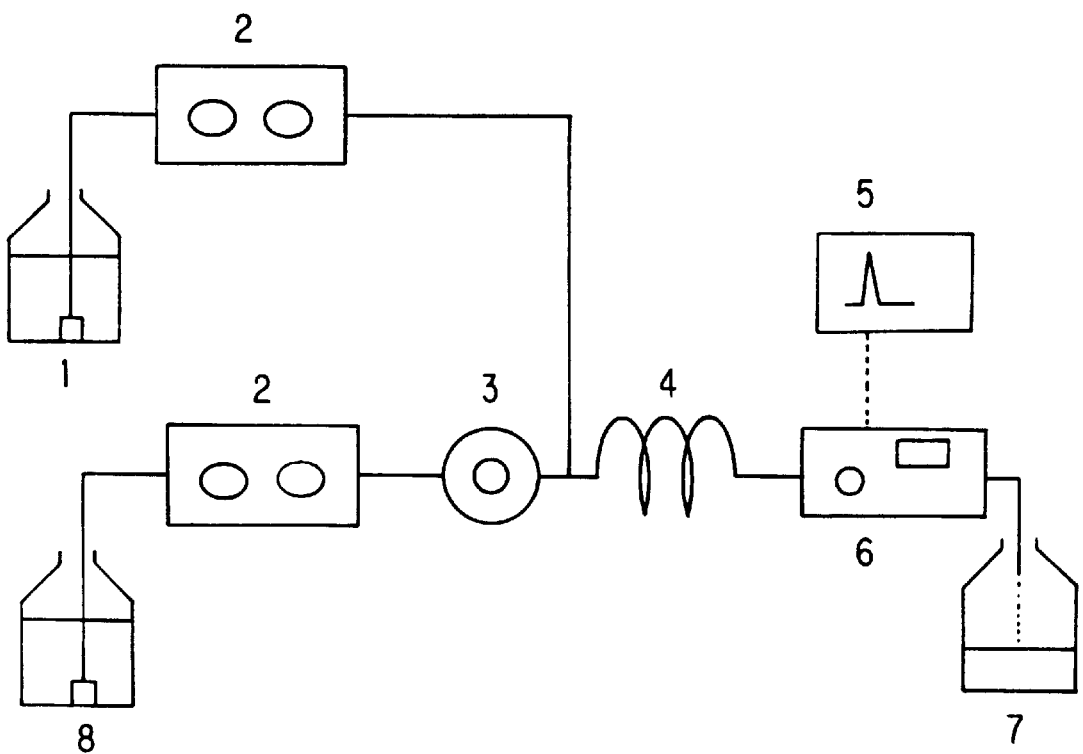
FIG. 2 shows another conventional system for measuring β-glucan content by a flow injection method using calcofluor.
Figure 3:
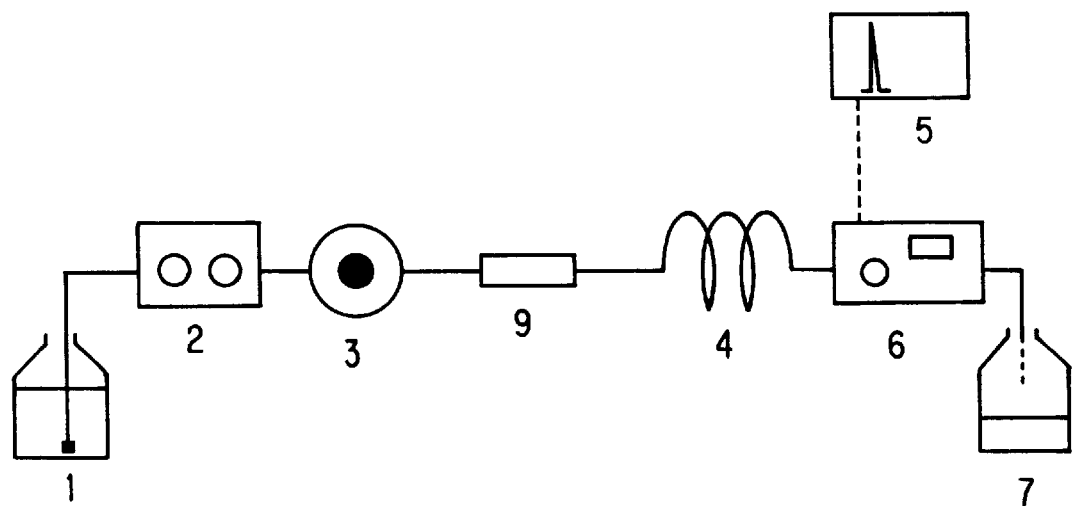
FIG. 3 shows one system employing a gel filtration column for measuring β-glucan content by a flow injection method using calcofluor.
Figure 4:
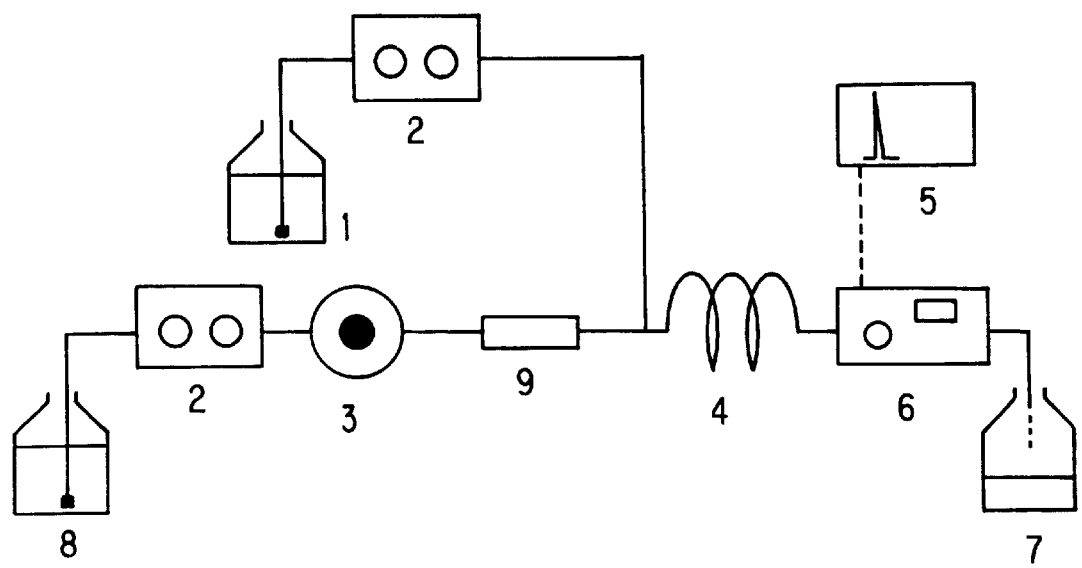
FIG. 4 shows another system employing a gel filtration column for measuring β-glucan content by a flow injection method using calcofluor.

The method according to the present invention employs the system shown in FIG. 3 and FIG. 4, to which conventional systems shown in FIG. 1 and FIG. 2 can be applied as they are.

In the method for measuring according to the present invention, types of the gel particles and column volume to be used are critical. When a gel filtration column for analytical use usually employed is employed, the sample elution time becomes too long (analysis requires 30 minutes or longer) to be suitable to the flow injection method whose advantage is a short time measurement. However, when the column volume is reduced excessively for the purpose of reducing the analysis time, then the separation between high molecular, β-glucan and maltose, ethanol and substances hindering fluorescent reaction of calcofluor may become unsatisfactory.

When target β-glucan is retained within the gel particle and eluted as being separated by molecular weights (being subjected to molecular sieve), the peak height varies depending on the molecular weight distribution of β-glucan in a sample such as wort or beer and leads to the measured values also varying depending on the molecular weight distribution, which are not acceptable in view of the purpose of the present invention which is to measure the total amount of high molecular β-glucan.

Accordingly, a gel filtration column is required to be capable of separating high molecular β-glucan from saccharides, ethanol and substance hindering fluorescent reaction of calcofluor within a short time period and to allow high molecular β-glucan to be eluted without being subjected to the molecular sieve effect.

Practically, since it is required in the flow injection method to elute high molecular β-glucan rapidly, the volume of the interstice outside of the gel particles in the column is desired to be small and required to be not larger than the volume of the effluent which is eluted from the column within a certain time period so as to allow high molecular β-glucan to pass through in a short period of time.

On the other hand, it is considered that the column content volume after packing the gel particles should be 10 times or more as large as the sample injection volume for the purpose of separation of low molecular saccharides, ethanol and substances hindering fluorescent reaction of calcofluor (from β-glucan).

In the examples described in the later part of this specification, the volume of the interstice outside of the gel particles is not larger than the column effluent volume per 1 minute for the purpose of completing the elution of high molecular β-glucan within 1 minute. Thus, HPLC analysis can be completed within 1 minute.

Also required is to use a gel particle having a limiting exclusion molecular weight of 4,000 to 300,000 in order to separate high molecular β-glucan from low molecular saccharides, ethanol and substances hindering fluorescent reaction of calcofluor without subjecting target high molecular β-glucan to the molecular sieve effect.

When a gel particle having a limiting exclusion molecular weight exceeding 300,000 is used, high molecular β-glucan in wort or beer is subjected to the molecular sieve effect and the elution is retarded, resulting in poor separation from low molecular saccharides, ethanol and substance hindering fluorescent reaction of calcofluor. When a gel particle having a limiting exclusion molecular weight lower than 4,000 is used, then the elution of low molecular saccharides, ethanol and substance hindering fluorescent reaction of calcofluor becomes earlier, resulting in poor separation from β-glucan.

For the reasons described above, the present invention usually employs a gel particle having a limiting exclusion molecular weight of 4,000 to 300,000, preferably around 100,000. Examples of such gel particles are Shodex OHpak SB-803 HQ (Trade name, produced by SHOWA DENKO K.K.) and Asahipak GS320 HQ (trade name, produced by SHOWA DENKO K.K.).

Also in the embodiment of the present invention, a column having a large number of theoretical plates (index of column separation performance) is suitably employed and a column having a number of theoretical plates not less than 10,000 is preferable.

In the method according to the present invention, although a system in which one pump as shown in FIG. 3 is used may also employ the column mentioned above, it may have disadvantage that passage of calcofluor or buffer for the calcofluor fluorescent reaction through the column causes reduced resolution or early deterioration of the column. Accordingly, as shown in FIG. 4, the system in which the flow for injecting and transporting the sample to the column is provided independently of the flow for transporting calcofluor and then after passing through the column the binding reaction of β-glucan with calcofluor is effected to is preferred.

The position at which the gel filtration column is placed in the system is someplace between the sample injection port and the detector, preferably between the sample injection port and the calcofluor reaction zone, where low molecular saccharides, ethanol and substances hindering fluorescent reaction of calcofluor in the sample are separated from β-glucan, and thereafter high molecular β-glucan-containing fraction eluted earlier is mixed with the calcofluor reaction fluid in the reaction zone, whereby detecting high molecular β-glucan.

In the method according to the present invention, the substances having inhibitory effects, saccharides and ethanol described above are also mixed with calcofluor after detection of β-glucan, and transported to the detector. Although negative peaks may be observed following the peak of β-glucan when the substances having inhibitory effects are contained in a large amount, such negative peaks are usually obscured by the tailing of the peak of β-glucan, exhibiting no particular apparent peaks.

It may also be possible that since the substances having inhibitory effects exhibit the negative peaks and maltose and ethanol exhibit positive peaks, there is no apparent peak as a result of counterbalancing each other.

As a fluid (solvent) for the flow in which a sample is transferred to the gel filtration column, any of those which cause no deterioration of the column and have no effects on the subsequent reaction of calcofluor with β-glucan, and typically distilled water is employed.

When a gel filtration column is installed in a device employing a flow injection system using calcofluor, it is required to maintain the atmosphere of the measurement (the room where the measurement is conducted) at a constant temperature, usually within the range from 10 to 40° C., preferably within 15 to 30° C.

The reason for the requirement of the temperature mentioned above is, as also explained in the later part of this specification, that if the atmospheric temperature during the measurement is changed the measured value of β-glucan is changed due to the variation in resolution performance of the column and in reactivity of low molecular β-glucan contained in the sample with calcofluor in response to the variation in atmospheric temperature.

EXAMPLE

The present invention is further illustrated more specifically by referring to the following examples.

Example 1

The system shown in FIG. 4 was employed in this example. Distilled water was used as the solvent to flow through the column, and 0.1 M glycine—NaOH buffer solution (pH 9.2) containing 20 mg/L calcofluor and 100 mg/L Triton X was used as the fluid to be mixed with the sample after passing through the column, both at the flow rate of 2 ml/min. The excitation wavelength of the detector employed was at 360 nm and the emission wavelength thereof was at 420 nm. 0.1 M Tris-HCl buffer (pH 8.2) may be employed instead of 0.1 M glycine -NaOH buffer.

The reaction zone was constructed with a Teflon tube having the inner diameter of 0.5 mm and the empty volume of 0.5 ml. The column having the inner diameter of 6.0 mm and the length of 50 mm was packed with gel particles "Shodex OHpak SB-803 HQ" produced by SHOWA DENKO K.K. (limiting exclusion volume: 100,000) (volume of the interstice outside of the gel particles: 0.5 ml, column content volume: 0.9 ml), to which 0.02 ml of the sample was injected.

Standard solutions were made from purified β-glucan extracted from barley by dissolving in distilled water at the concentrations of 30 mg/L, 50 mg/L, 75 mg/L, 100 mg/L, 150 mg/L, 200 mg/L and 250 mg/L, and calibration curve was made from the peak height of the standard solutions measured.

Sample A was made by adding β-glucanase to beer to decompose β-glucan in the beer followed by inactivating β-glucanase by heating to obtain a β-glucan-free beer followed by dissolving barley β-glucan at 100 mg/L in the β-glucan-free beer, Sample B was made by dissolving barley β-glucan at 100 mg/L in the β-glucan-free wort made similarly, Sample C was made by dissolving barley β-glucan at 100 mg/L in 10% (w/v) aqueous solution of maltose, and Sample D was made by dissolving barley β-glucan at 100 mg/L in 5% (v/v) aqueous ethanol. The peak height of each sample was measured and β-glucan content in each sample was determined referring to the calibration curve made as described above. The results are shown in Table 1. The atmospheric temperature (temperature around the device) was 20° C.

TABLE 1

Effect of measurement condition on glucan content (ppm)

| | β-glucan content (ppm) | | | |
|---|---|---|---|---|
| Sample | Example 1 | Comp. Example 1 | Comp. Example 2 | Comp. Example 3 |
| Sample A | 100 | 81 | 83 | 84 |
| Sample B | 101 | 84 | 86 | 86 |
| Sample C | 101 | 110 | 104 | 111 |
| Sample D | 100 | 108 | 103 | 107 |

Example 2

Wort E and beer F were employed as the samples and subjected to the measurement similarly as in Example 1 at predetermined atmospheric temperatures (temperature around the device was 18, 22 or 25° C.), and β-glucan contents in the samples were determined referring to the calibration curve made from the standard solutions similar to those in Example 1. The results are shown in Table 2.

TABLE 2

Change in β-glucan content (ppm) at varying atmospheric temperature

| Atmospheric Temperature | Sample | β-glucan content (ppm) | |
|---|---|---|---|
| | | Example 2 | Example 3 |
| 18° C. | Wort E | 110 | 107 |
| | Beer F | 203 | 194 |
| 22° C. | Wort E | 102 | 107 |
| | Beer F | 185 | 193 |

TABLE 2-continued

Change in β-glucan content (ppm) at varying atmospheric temperature

| Atmospheric Temperature | Sample | β-glucan content (ppm) | |
|---|---|---|---|
| | | Example 2 | Example 3 |
| 25° C. | Wort E | 99 | 106 |
| | Beer F | 178 | 194 |

Example 3

Wort E and beer F was employed as the samples similarly as in Example 2, and the entire system was placed in a chamber maintained at 20° C. Otherwise, the similar manner was employed as in Example 1 to measure the peak heights, from which β-glucan contents in the samples were determined referring to the calibration curve made from the standard solutions similar to those in Example 1. The results are shown in Table 2.

Comparative Example 1

Except for employing the system shown in FIG. 2 and installing no gel filtration column, the peak heights of Sample A to D were measured similarly as in Example 1, and β-glucan contents in the samples were determined referring to the calibration curve made from the standard solutions similar to those in Example 1. The results are shown in Table 1.

Comparative Example 2

Except that the sample injection volume was 0.1 ml, the peak heights of Sample A to D were measured in the system and condition similar to those in Example 1, and β-glucan contents in the samples were determined referring to the calibration curve made from the standard solutions similar to those in Example 1. The results are shown in Table 1.

In this case, the column content volume was 0.9 ml, which corresponded to the volume 9 times as large as the sample injection volume.

Comparative Example 3

Except for employing Shodex OHpak SB-804 HQ (limiting exclusion molecular weight: 2,000,000) produced by SHOWA DENKO K.K. as the gel filtration particle, the peak heights of Sample A to D were measured in the system and condition similar to those in Example 1, and β-glucan contents in the samples were determined referring to the calibration curve made from the standard solutions similar to those in Example 1. The results are shown in Table 1.

As evident from the results shown in Table 1, the measured values in Example 1 were 100 mg/L or the values very close thereto as expected theoretically, while the measured values in Comparative Examples were lower or higher than the theoretical value due to unsuccessful or unsatisfactory separation of β-glucan from maltose, ethanol and substances hindering fluorescent reaction of calcofluor.

Therefore, it was indicated that by using a gel filtration column fulfilling certain requirements it is possible to separate β-glucan from the low molecular substances in beer or wort causing fluctuation in the measured values as the factors and to perform more accurate measurements.

Also as evident from the device and condition in Example 1, it was possible to complete the measurement of one sample within 1 minute, and, taking the sample injection step into consideration, it was proven that the measurement time is not different from that by a conventional device employing substantially no column.

As shown in Table 2, by maintaining the entire device at a constant temperature, constant measured values regardless of the room temperature can be obtained, whereby achieving a higher accuracy.

Thus, the atmospheric temperature during measurement should be constant. In addition, the atmospheric temperature should be the same and constant when the same measurement is repeated.

Example 4

The experiment was conducted similarly as in Example 1 except that distilled water was employed as the solvent to flow through the column at the flow rate of 1 ml/min, calcofluor as the fluid to be mixed after passing through the column at the flow rate of 2 ml/min, the reaction zone was constructed from a Teflon tube having the inner diameter of 0.5 mm whose empty volume had been modified to a predetermined value, and the injection volume was 0.005 ml.

Figure 5:
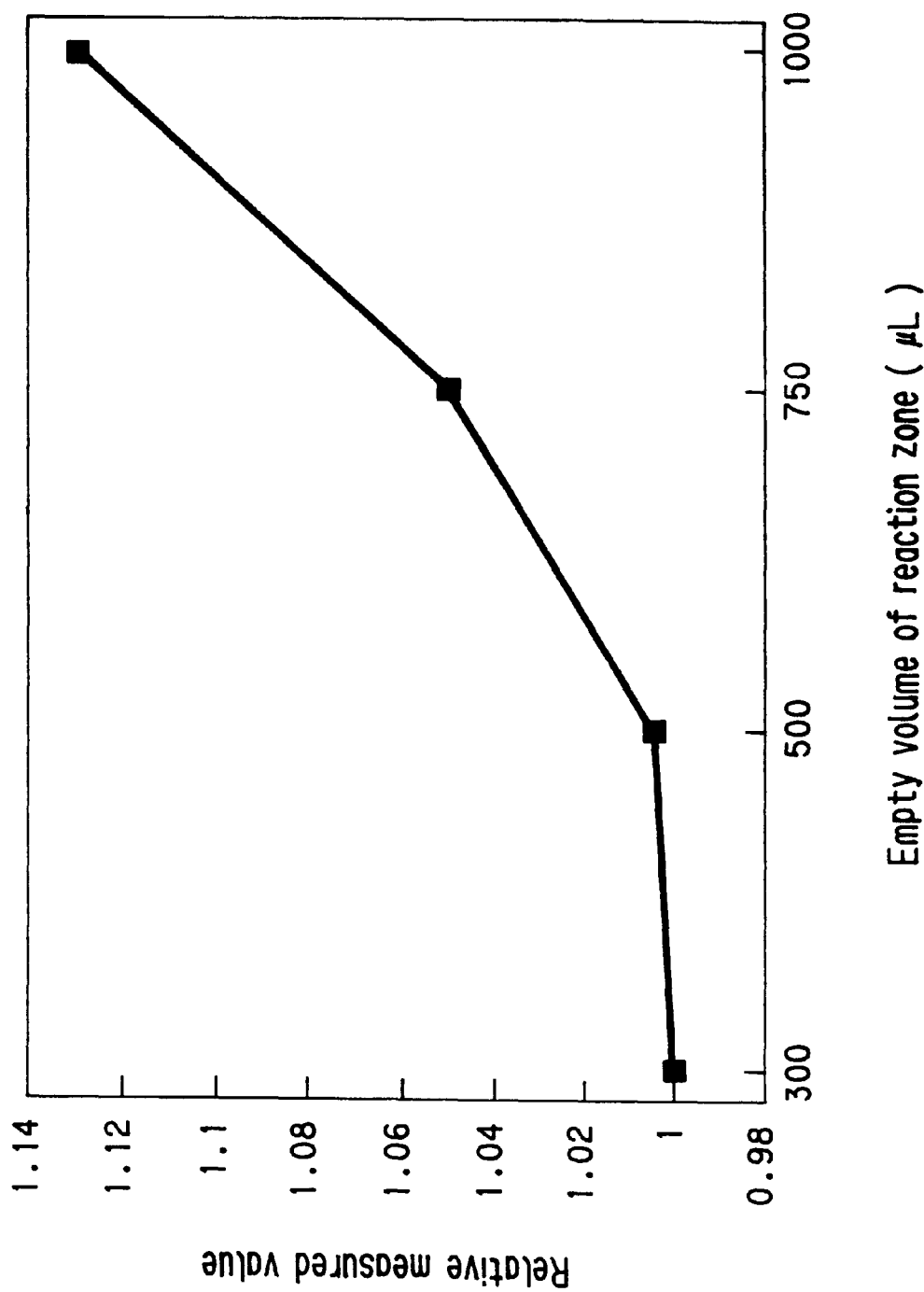
FIG. 5 shows the effects of the empty volume in the reaction zone in the method according to the present invention.

The measurement was conducted with varying empty volume of the reaction zone. The results are shown in FIG. 5.

The ordinate in the figure represents the relative value based on the measured value=1 with the empty volume of the reaction zone of 300 $\mu$l. As evident from the figure, no variation in the measured value was observed with the empty volume of 500 $\mu$l or less, possibly because a longer mixing tube allows high molecular β-glucan once separated to combine again with low molecular β-glucan.

Example 5

Figure 6:
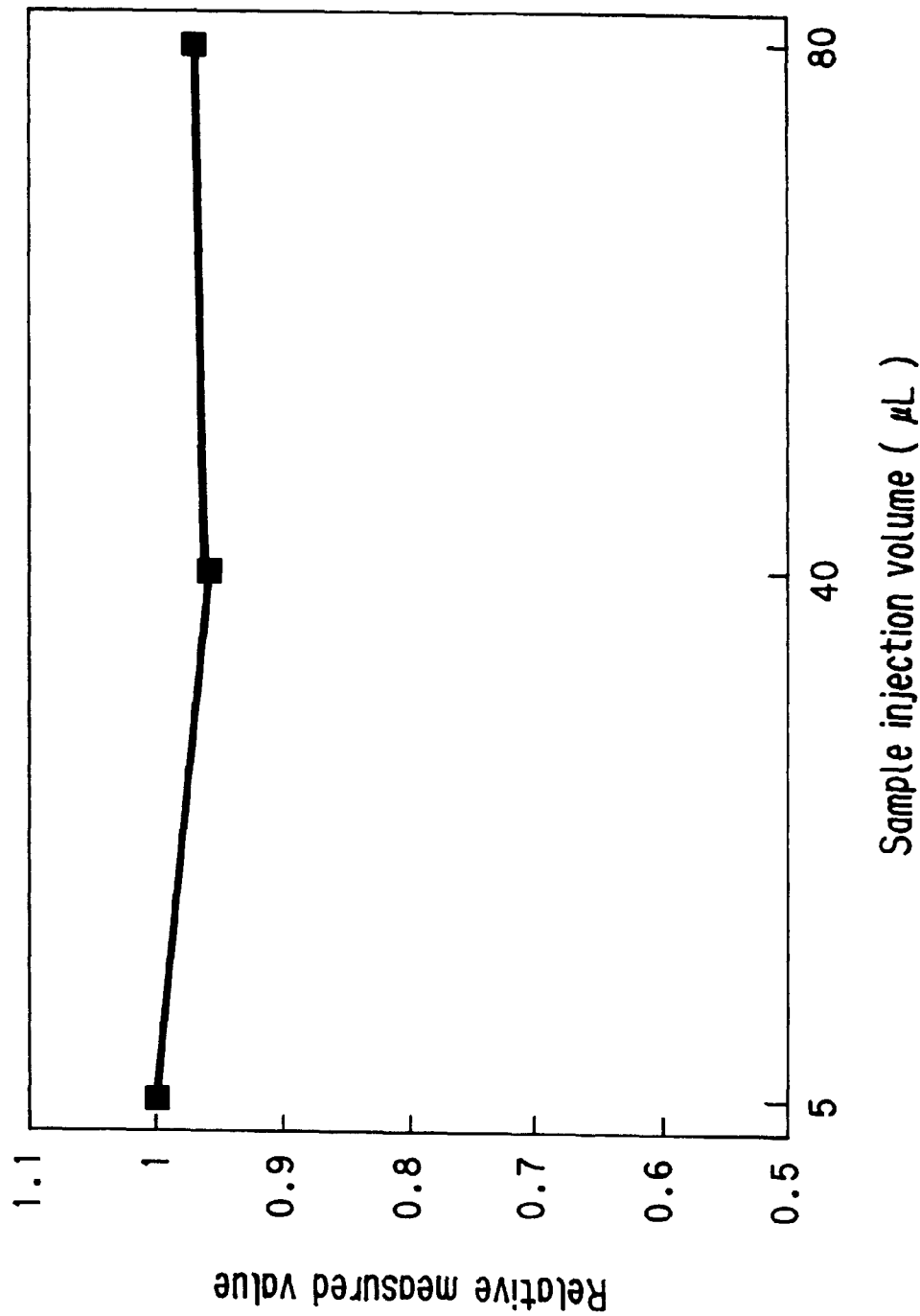
FIG. 6 shows the effects of the sample injection volume in the method according to the present invention.

Under the condition similar to that in Example 4, the measurement was conducted with the empty volume of 0.5 ml and the sample injection volume varying from 5 $\mu$l to 80 $\mu$l. The results are shown in FIG. 6. The ordinate in the figure represents the relative value based on the measured value=1 with the sample injection volume of 5 $\mu$l. As evident from the figure, almost no error occurred when the sample injection volume was increased to about 80 $\mu$l. Thus, by limiting the sample injection volume to $\frac{1}{11}$ or less in relation to 900 $\mu$l of the column content volume (the column content volume is 11 times or more as large as the sample injection volume), almost no fluctuation in the measured value was observed.

possibility of Industrial Utilization

According to the method of the present invention, β-glucan content in a sample can be determined at a high accuracy and reproducibility without being affected by low molecular saccharides such as maltose, ethanol and substances hindering fluorescent reaction of calcofluor all contained in the sample. Therefore, β-glucan content in a sample such as various cereals, malt extract, and beer can be compared and evaluated reliably.

I claim:

1. A method for measuring the concentration of β-(1,3)(1,4)-D-glucan in a sample, comprising:
   introducing, into a flow-injection system comprising a sample injection port, a gel filtration column, and a detector:
   (i) a sample comprising β-(1,3)(1,4)-D-glucan and lower molecular weight components; and (ii) a reaction solution comprising calcofluor;

passing said sample through said column to elute a unretained β-glucan within about one minute, while the low molecular weight components are retarded from passing through the column, wherein said column comprises:
  (a) gel particles having a limiting exclusion molecular weight of 4,000–300,000;
  (b) the filtration column has a void or interstitial volume that is not larger than an effluent volume eluted from the column within one minute; and
  (c) a column content volume that is at least 10 times greater than the volume of the sample;

allowing said calcofluor to bind to said unretained β-glucan; and measuring the concentration of said β-glucan.

2. The method for measuring β-(1,3)(1,4)-D-glucan according to claim 1 wherein the zone around the system during measurement is kept at a predetermined constant temperature.

3. The method according to claim 2, wherein said temperature is 10–40° C.

4. The method according to claim 1, wherein said lower molecular weight components comprise saccharides and/or ethanol.

5. The method according to claim 1, wherein said sample is passed with a column solvent through said column prior to binding to said calcofluor.

6. The method according to claim 5, wherein said column solvent is distilled water.

* * * * *